United States Patent [19]
Matson

[11] Patent Number: 6,037,124
[45] Date of Patent: Mar. 14, 2000

[54] CARBOXYLATED POLYVINYLIDENE FLUORIDE SOLID SUPPORTS FOR THE IMMOBILIZATION OF BIOMOLECULES AND METHODS OF USE THEREOF

[75] Inventor: Robert S. Matson, Orange, Calif.

[73] Assignee: Beckman Coulter, Inc., Fullerton, Calif.

[21] Appl. No.: 08/720,307

[22] Filed: Sep. 27, 1996

[51] Int. Cl.[7] .................................................. C12Q 1/68
[52] U.S. Cl. ........................... 435/6; 422/50; 422/68.1; 436/501; 530/333; 536/25.3
[58] Field of Search .................................. 435/6, 7.5, 7.1; 536/24.3, 25.3; 436/172, 501; 525/326.2; 422/50, 68.1; 530/333

[56] References Cited

U.S. PATENT DOCUMENTS 4,775,619 10/1988 Urdea .......................................... 435/6
5,011,861 4/1991 Coull et al. ................................ 521/53
5,602,207 2/1997 Boyd et al. ........................... 525/326.2

OTHER PUBLICATIONS

Chehab et al., Hum. Genet. 89:163–168, 1992.
Lee et al., Journal of Virol. Methods 33:217–222, 1991.
Matthews et al., Anal. Biochem. 169:1–25, 1988.

*Primary Examiner*—Ardin H. Marschel
*Attorney, Agent, or Firm*—William H. May; Margaret A. Kivinski

[57] ABSTRACT

The present invention relates to a method of immobilizing oligonucleotides and other biomolecules using a carboxylated polyvinylidene fluoride support membrane for the construction of geosensors and other array-based systems. The support membrane may be used in either covalent or non-covalent binding states.

20 Claims, 5 Drawing Sheets

5' AMINO OLIGONUCLEOTIDE - LINKED

STREPTAVIDIN - LINKED

COVALENT IMMOBILIZATION OF BIOMOLECULES

NON-COVALENT IMMOBILIZATION OF
STREPTAVIDIN-OLIGONUCLEOTIDES

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 16 base pairs (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:1:

ACCAAAGATG ATATTT                                                    16

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: YES (xi) SEQUENCE DESCRIPTION: SEQ ID NO:2:

AAATATCATC TTTGGTGT                                                  18

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:3:

CACACCAAAG ATGATATTT                                                 19

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (iii) HYPOTHETICAL: NO (iv) ANTI-SENSE: NO (xi) SEQUENCE DESCRIPTION: SEQ ID NO:4:

ACACCGCCGG                                                           10

(2) INFORMATION FOR SEQ ID NO:5:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE:  DNA (iii) HYPOTHETICAL:  NO (iv) ANTI-SENSE:  NO (xi) SEQUENCE DESCRIPTION:  SEQ ID NO:5:

ACACCGACGG C                                                                              11

(2) INFORMATION FOR SEQ ID NO:6:

(i) SEQUENCE CHARACTERISTICS:
            (A) LENGTH:   20 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  NO (iv) ANTI-SENSE:  NO (xi) SEQUENCE DESCRIPTION:  SEQ ID NO:6:

GACGGAATAT AAGCTGGTGG                                                                     20

(2) INFORMATION FOR SEQ ID NO:7:

(i) SEQUENCE CHARACTERISTICS:
            (A) LENGTH:   20 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  NO (iv) ANTI-SENSE:  NO (xi) SEQUENCE DESCRIPTION:  SEQ ID NO:7:

CTCTATAGTG GGGTCGTATT                                                                     20

(2) INFORMATION FOR SEQ ID NO:8:

(i) SEQUENCE CHARACTERISTICS:
            (A) LENGTH:   109 base pairs
            (B) TYPE:  nucleic acid
            (C) STRANDEDNESS:  single
            (D) TOPOLOGY:  linear (ii) MOLECULE TYPE:  DNA (iii) HYPOTHETICAL:  NO (iv) ANTI-SENSE:  YES (xi) SEQUENCE DESCRIPTION:  SEQ ID NO:8:

CTCTATAGTG GGGTCGTATT CGTCCACAAA ATGGTTCTGG ATCAGCTGGA                                     50

TGGTCAGCGC ACTCTTGCCC ACACCGCMGG CGCCCACCAC CACCAGCTTA                                    100

TATTCCGTC                                                                                109

(2) INFORMATION FOR SEQ ID NO:9:

(i) SEQUENCE CHARACTERISTICS:
            (A) LENGTH:   109 base pairs
            (B) TYPE:  nucleic acid
            (C) STRANDEDNESS:  single -continued

```
       (D) TOPOLOGY:  linear (ii) MOLECULE TYPE:  DNA (iii) HYPOTHETICAL:  NO (iv) ANTI-SENSE:  NO (xi) SEQUENCE DESCRIPTION:  SEQ ID NO:9:

GACGGAATAT AAGCTGGTGG TGGTGGGCGC CGKCGGTGTG GGCAAGAGTG                   50

CGCTGACCAT CCAGCTGATC CAGAACCATT TTGTGGACGA ATACGACCCC                  100

ACTATAGAG                                                               109
```

CARBOXYLATED POLYVINYLIDENE FLUORIDE SOLID SUPPORTS FOR THE IMMOBILIZATION OF BIOMOLECULES AND METHODS OF USE THEREOF

BACKGROUND OF THE INVENTION

1. Field of the Invention

The present invention relates to the use of materials for immobilizing oligonucleotides and other biomolecules for the construction of genosensors and other array-based systems. The use of the materials according to the present invention allows for the attachment of previously synthesized oligonucleotides and other biomolecules at high ligand densities with low background fluorescence and non-specific adsorption.

2. Description of the Prior Art

Nucleic acid hybridization assays have been used extensively in molecular biology to establish the sequence similarity of populations of nucleic acids. Hybridization is simply the annealing or pairing of single stranded nucleic acid molecules (DNA or RNA) to form double strands. The most common modern technique employing hybridization is the Southern blot hybridization, invented by Dr. E. Southern (1) in which a set of unknown target DNA molecules is immobilized on a membrane and a labeled probe DNA molecule in solution is used to bathe the membrane under conditions where complementary molecules will anneal. In an analogous technique called Northern blot hybridization (2,3). RNA molecules immobilized on membranes are the targets. The labeled probe DNA used in the liquid phase can be as short as 10–20 nucleotides: probes are usually labeled with radioisotopes, although other reporter groups (e.g., fluorescein, biotin, etc.) can be used. Reverse blot hybridization employs the opposite approach. Instead of immobilizing unknown DNAs, a set of well defined DNA probes are immobilized on a solid surface, and unknown labeled "target" DNA is present in the liquid phase. Therefore, in reverse hybridizations a large number of probes can be used with single target molecules. By decoding the hybridization pattern of the unknown DNA to positions of known sequence on the solid phase array, sequence information from several positions of the unknown target DNA can be obtained.

The first interest in reverse hybridization was spurred by the idea that oligonucleotide probes could be used to sequence unknown DNA samples by observing the pattern of positive hybridization to all possible oligonucleotide sequences of a fixed length (refs. 4–8). The speed of the assay and its potential for automation compared with existing sequencing techniques has generated much excitement in the genome sequencing community. However, the ability to assay shorter known DNA segments for the sequence alterations by reverse hybridization appears to be a more practical application at present.

There are two fundamental ways of generating oligonucleotide arrays: the oligonucleotides may be synthesized on the solid phase in their respective positions, or they may be synthesized apart from the surface of the array matrix and attached later. The former method has been successfully achieved in several different ways. The first reverse hybridization arrays to be synthesized in situ were made by Dr. Southern, using glass modified with an aliphatic poly(ether) linker as a solid support (9).

Alternatively, unique sets of photosensitive protecting groups have also been used during DNA synthesis to selectively build reverse hybridization arrays. In this photolithographic technique, light is used to unmask specific hydroxyl groups within the growing array to sequentially add the desired bases (10).

The immobilization of previously synthesized oligonucleotides has been approached in different ways. In general, the attachment of standard oligonucleotides to unmodified glass or plastic surfaces is inefficient. For this reason, most investigators trying to immobilize oligonucleotides modify them with molecules that promote adsorption or enable covalent attachment to the support. Oligonucleotides modified with bovine serum albumin adsorb passively to microliter plates designed to bind protein molecules (11). Biotinylated oligonucleotides bind tightly to plates or beads that are coated with avidin or streptavidin. Oligonucleotides with polythymidylate tails have been photochemically crosslinked to nylon (12). More recently, oligonucleotides with terminal amino (13,14) or methyluridine (15) groups have been covalently crosslinked to compatible reactive groups on multi-well plate surfaces.

Both approaches to array construction have different advantages. Synthesis in situ does not involve handling thousands or tens of thousands of independent oligonucleotides, each of which must be produced on a scale that far exceeds that which is required for the array. In contrast, the ability to freely arrange the members of an array after oligonucleotide synthesis is only possible with pre-synthesized oligonucleotides. Matson et al., has recently published two papers on the development of surface chemistry for reverse hybridization arrays and on the use of arrays to detect DNA sequence repeats in a variety of target DNA's. In the first paper (16), the authors examine the feasibility of using polypropylene as a support for the construction of reverse hybridization arrays. In addition to being easy to handle, a good support must possess several important properties; it must be stable under the conditions of harsh organic synthesis encountered during DNA synthesis, while having low non-specific binding of DNA during aqueous hybridization. It is also advantageous for the support to have low fluorescent background for sensitive non-radioactive detection. Native polypropylene possesses all of these qualities, but DNA synthesis cannot be done on the unmodified polymer. Matson et al. used radio-frequency plasma discharge in the presence of ammonia gas to aminate the polypropylene surface. The amino group offers a sufficiently active nucleophile to promote nucleic acid base coupling to the support using the conventional CED-phosphoramidite chemistry employed to synthesize oligonucleotides on modern DNA synthesizers including the Beckman Oligo 1000. Oligonucleotides synthesized on aminated polypropylene when released from the support were found to be of excellent quality, a prerequisite for use in further hybridization experiments.

While most hybridization assays rely on detecting signals from DNA molecules while they are still bound to their targets, the desorption (dissociation of "melting") profile may also be used to differentiate complementary and mismatched hybridizations. Matson et al. devised an elution system using a modified flow-cell and radioisotope detector with a Beckman Model 126 HPLC gradient system. Small pieces of hybridized polypropylene membrane or threads on which a single oligonucleotide probe sequence was synthesized were placed in the flow cell and the previously annealed target DNA was slowly eluted using a decreasing linear salt gradient. Using test oligonucleotide targets, the dissociation of a short target from the complementary oligonucleotide covalently bound to the support was slightly faster for a target with a single nucleotide mismatch and much faster for a target containing a two nucleotide detection. More importantly, a target derived from a cystic fibrosis patient was shown to have a dramatically different elution profile than a target from a normal individual. In addition to obtaining information on the dissociation process, the dynamic hybridization analysis system is also a way that designers of reverse hybridization arrays can optimize the buffer conditions to obtain binding of perfectly matched nucleic acid sequences.

The second paper, done in collaboration with Drs. Manfred Wehnert and Thomas Caskey from Baylor College of Medicine (17), uses reverse hybridization arrays to identify the presence of dinucleotide and trinucleotide repeats in PCR amplified DNA samples. These repeats, along with tetranucleotide repeats, comprise the class of DNA sequences called short tandem repeats or STR's which are dispersed throughout the human genome. STR's are generally found in regions of the genome that do not code for proteins and they often vary in copy number and therefore overall length between individuals. These variations in size (STR polymorphisms) usually do not cause any harmful effects. By comparing the size of repeats at specific locations in divergent individuals, the polymorphisms can be used to track the inheritance of specific gene segments and in this way they can be used just like restriction fragment length polymorphisms (18) to predict disease status to map unknown genes and to identify individuals.

However, in a few important chromosomal locations where the repeats have been found within genes, an increase in repeat size has been shown to cause disease. Huntington's Disease (19) and the fragile X mental retardation syndrome (20–22) are two important examples. Thus, it is useful to identify molecular clones of genomic DNA that carry these repeated sequences. Wehnert et al. demonstrates that using both DNA sequences known to contain specific dinucleotide and trinucleotide repeats, and a cosmid alone that contains unknown repeats as targets, one can obtain hybridization signals that reflect the presence of these repeats.

As mentioned above, there are many supports that will bind nucleic acids. However, few of these are suitable for the attachment of small oligonucleotides (10mer to 20mer) at sufficient ligand density to be useful for hybridization and detection of complementary target nucleic acids. Moreover, commercially available DNA binding membranes currently available suffer from high background fluorescence and non-specific adsorption. A need therefore still exists for support materials which bind small oligonucleotides which have low intrinsic background fluorescence and low non-specific adsorption properties.

SUMMARY OF THE INVENTION

The preceding and other shortcomings of the prior art are addressed and overcome by the present invention which provides, in a first aspect, a method for using carboxylated polyvinylidene fluoride (PVDF) substrate surfaces for the immobilization of oligonucleotides and other biomolecules. More particularly, the present invention provides analytical methods which include providing a solid support fabricated of carboxylated polyvinylidene fluoride having oligonucleotide probes bound to the surface and applying sample which may contain oligonucleotide targets to the surface under hybridizing conditions. By detecting if hybridization occurs the presence or absence of oligonucleotide targets in the sample is determined.

In a specific embodiment of the present invention, a carboxylated PVDF support is first activated by reacting carboxyl groups with suitable reagents to form reactive functional groups, e.g. reactive carboxylic esters, which promote the attachment of reactive nucleophilic groups present on derivatized oligonucleotides or other biomolecules. Following covalent coupling of the a biomolecule probe to the activated support, hybridization of a complementary target biomolecule can be detected using a variety of different detection approaches. For example, the complementary target can be biotinylated and the detection accomplished using a streptavidin (or other binding proteins)-conjugate label or reporter system. Another approach involves labeling the complementary target with a direct reporter such as a radioisotope or fluorescent tag.

In a similar method, streptavidin or other similar binding protein can be linked covalently to a PVDF support by various coupling chemistries through available reactive amino acid residues of the binding protein. The binding protein can then be used to bind oligonucleotide probes making them available for hybridization with a suitable oligonucleotide target.

Another embodiment of the present invention involves analytical methods which include reacting a biomolecule binding protein with a biomolecule to form a biomolecule complex, the biomolecule being capable of specifically binding with a target biomolecule which may be present in an analytical sample. Then applying the biomolecule complex to a carboxylated polyvinylidene fluoride substrate, results in an immobilized biomolecule complex. Finally, applying a sample to the immobilized biomolecule complex; and detecting the presence of target biomolecules specifically bound to the immobilized biomolecule determines the presence or absence of the target biomolecules in the sample. In preferred embodiments, the biomolecules are biotinylated oligonucleotides and the biomolecule binding protein is avidin or streptavidin.

In another aspect the present invention provides target biomolecule analysis methods which include forming a biomolecule probe by reacting a biomolecule binding protein with a biomolecule, the biomolecule being capable of specifically binding with the target biomolecule. Then contacting the biomolecule complex with a sample under conditions suitable for specifically binding any target biomolecule present in the sample with the biomolecule probe results in a second complex. The next step involves reacting a second biomolecule having an attached reporter group with the second complex, the second biomolecule being capable of specifically binding with at least a portion of any bound target biomolecule, thereby forming a third complex. Then, applying the third biomolecule complex to a carboxylated polyvinylidene fluoride membrane, results in the formation of an immobilized third biomolecule complex. Finally, detecting the reporter group on the immobilized third biomolecule complex confirms the presence of any target biomolecules specifically bound to the biomolecule probe. In preferred embodiments the biomolecule, biomolecule target and the second biomolecule are oligonucleotides and the binding protein is avidin or streptavidin.

The present invention additionally provides reagents which include carboxylated polyvinylidene fluoride having immobilized biomolecules. The biomolecules can be immobilized through covalent attachment or through non-covalent interactions such as via binding proteins and their specific binding partners. Covalent interactions include reacting the biomolecule with carboxylate functionalities or activating the PVDF by forming highly reactive functionalities on the surface of the PVDF. The highly reactive functionalities are capable of reacting with biomolecules. Non-covalent interactions of binding proteins and their specific binding partners are possible due to the surprising discovery that binding proteins will become strongly attached to PVDF surfaces without a covalent link. Thus, for example streptavidin will bind to PVDF surfaces providing a site for immobilizing biotinylated biomolecule probes through streptavidin-biotin binding. Biomolecules such as oligonucleotides, peptide-nucleic acids (PNAs), proteins, peptides, carbohydrates, lipids and small organic and organo-metallic ligands can be attached to one member of the specific binding partner, for example biotin, while the other member is immobilized on a film, membrane or solid support device of carboxylated PVDF. In addition to the avidin/streptavidin and biotin interaction other specific binding interactions are also suitable for immobilizing biomolecules to carboxylated PVDF.

The foregoing and additional features and advantages of this invention will become apparent from the detailed description and accompanying drawing figures that follow.

DETAILED DESCRIPTION OF THE PREFERRED EMBODIMENTS

In accordance with the present invention, a method is provided for using solid supports fabricated of carboxylated polyvinylidene fluoride (PVDF) for the immobilization of oligonucleotides and other biomolecules. As used herein, the term "carboxylated polyvinylidene fluoride" or "carboxylated PVDF" means polyvinylidene fluoride having carboxyl groups. The terms "activated carboxylated PVDF", "activated carboxyl", and "activated PVDF" refer to highly reactive functionalities, formed by reacting the carboxyl groups on the PVDF support surface with suitable reagents to form active groups, such as active esters, acyl fluorides, acyl azides, or hydrazides. Carboxylated PVDF solid supports in the form of thin membranes are preferred in the practice of the present invention. However, solid supports in the form of non-porous films sheets, threads, beads and molded or formed three dimensional shapes are suitable.

Figure 1:
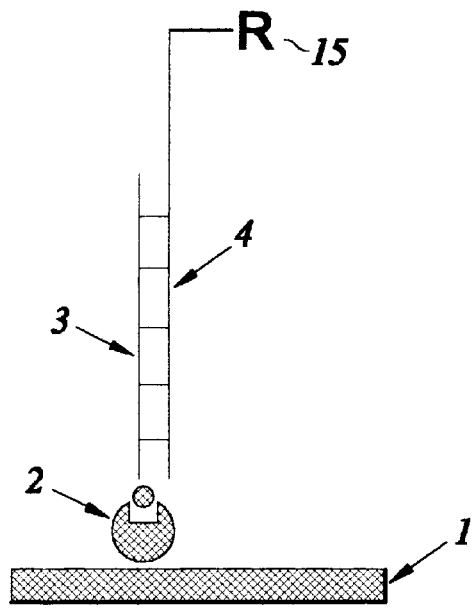
FIG. 1 is a graphical representation of the use of a carboxylated PVDF membrane support in accordance with one embodiment of the method of the invention.

A specific embodiment of the present invention is outlined in FIG. 1 wherein the various steps of the embodiment are illustrated. The first step involves applying streptavidin to a carboxylated PVDF solid support surface (1), resulting in non-covalently immobilized streptavidin to the carboxylated PVDF surface (2). While streptavidin or avidin is a preferred binding protein other binding proteins capable of sufficiently strong non-covalent interactions with carboxylated PVDF are suitable as well. Then applying biotinylated oligonucleotide (3) to the support surface (1) provides an immobilized oligonucleotide probe bound to the carboxylated PVDF surface via the strong biotin-streptavidin association. By applying a sample containing target nucleic acid molecule or target oligonucleotide (4) having an attached label or reporter group (15) to the carboxylated PVDF solid support under hybridizing conditions an oligonucleotide probe-oligonucleotide target complex forms when they are sufficiently complementary. Following a thorough rinsing, if the target oligonucleotide is sufficiently complementary to hybridize or anneal to the oligonucleotide probe the presence of the target in the sample is determined by detecting the label or reporter group. Labels and reporter groups which may be used in the practice of the invention include those that can be directly attached to the target biomolecule such as biotin and fluorescent dyes via internal labeling (e.g., biotin-dUTP or dCTP conjugate) during PCR; or end-labeled from incorporation of tagged primers. It is also possible to perform a sandwich hybridization in which an additional oligonucleotide complementary to the target is employed that contains the label or reporter. The following general labels/reporter groups are suitable in the practice of the present invention: chemiluminescent compounds (dioxetanes, acridinium esters, luminol, and the like); enzymes (alkaline phosphatase, horseradish peroxidase, luciferase, and the like); fluorescent compounds (ethidium, cyanine dyes, europium chelates, fluorescein, LaJolla Blue, rodamine, terbium chelates, etc.), metal complexes such as colloidal gold, latex particles, photoproteins (such as Aequorin and the like), haptens (biotin, digoxigen with anti-digoxigen, and the like) and radioluminescent compounds ($^{32}P$, $^{35}S$, and the like), and the like.

Those skilled in the art will appreciate that multiple probes can be applied to the surface of the carboxylated PVDF solid support at site specific locations. When each oligonucleotide probe is a different known oligonucleotide sequence and the site specific location is known for that sequence, multiple oligonucleotide tests can be performed. Thus, the presence of mutant or wild type DNA associated with a number of different infectious diseases or genetic diseases can be tested in a single test cycle. By detecting the presence of a reporter group at a specific location on such oligonucleotide "arrays", the presence or absence of the oligonucleotide target complementary to the probe is determined.

Figure 2:
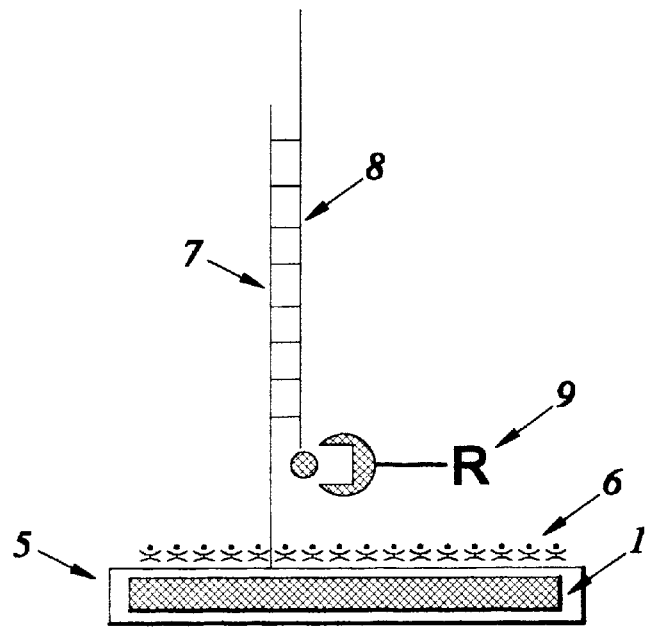
FIG. 2 is a graphical representation of the use of an activated, carboxylated PVDF support in accordance with another embodiment of the method of the invention.

A second method of the present invention is outlined in FIG. 2 wherein the various steps of the method are illustrated. Referring to FIG. 2, a carboxylated PVDF solid support (1) is first activated through its pendent carboxyl groups (5). In preferred embodiments, active esters are formed by reacting carboxyl groups with a suitable reagent such as carbodiimides (EDAC, DDC or the like), with or without NHS as a catalyst. Alternatively, the activated support can be converted to acid halides (O=C—X, where X=I, Br, Cl, F); other active esters (NHS, p-nitrophenyl, and the like); or transformed into acyl azides (O=C—N$_3$) from the hydrazide (O=C—NH—NH$_2$R) which is also an active intermediate. The activation provides active sites (6) which promote the attachment of reactive nucleophilic groups found on derivatized oligonucleotides e.g., an oligonucleotide labeled at its 5' or 3' terminus with an amino functionality. (7). Following covalently coupling a derivatized oligonucleotide probe (7) to an activated support (5) to form covalently immobilized oligonucleotide probes, applying a sample containing labeled target oligonucleotides (8) under hybridizing conditions will result in the oligonucleotide probe and the oligonucleotide target forming a complex when they are sufficiently complementary. After thoroughly washing the carboxylated PVDF surface, detecting the presence of the label determines the presence of complementary oligonucleotide target in the sample. The label can be a streptavidin-conjugate label or other reporter system (9). Other labels and reporter groups are described above. Streptavidin-conjugates include: alkaline phosphatase, horseradish peroxidase, FITC, Cy5, gold nanoparticles.

The above-described oligonucleotide arrays can be prepared using activated carboxylated PVDF surfaces by utilizing masking techniques to activate selected site specific portions of the carboxylated PVDF surface. Subsequently directing the attachment of specific known oligonucleotide probes to specific sites provides the oligonucleotide probe array.

Those skilled in the art will recognize that it is also possible to covalently link streptavidin (2) or other oligonucleotide binding proteins to the support (5) by various coupling chemistries through available reactive amino acid residues of the protein, such as lysyl groups. Streptavidin is void of any carbohydrate moiety and therefore is generally attached to supports via available amine containing amino acid residues (typically lysyl residues) to the activated carboxyl surface. For example, the carboxyl groups on a the support can be activated with EDAC/NHS and the streptavidin applied to the surface under basic conditions in an appropriate buffer (e.g., bicarbonate buffer, pH 8–9). For other oligonucleotide binding proteins containing carbohydrate groups, these may be immobilized by first oxidizing the sugar's glycosidic bond to aldehydes by periodate; followed by reaction with membrane carboxyl groups which have previously been converted to reactive hydrizides. Coupling is achieved at a neutral pH. If free sulfhydryl groups on the protein are available (cysteine residues) then the protein may be coupled to maleimide derivatized membrane carboxyl groups.

Figure 3:
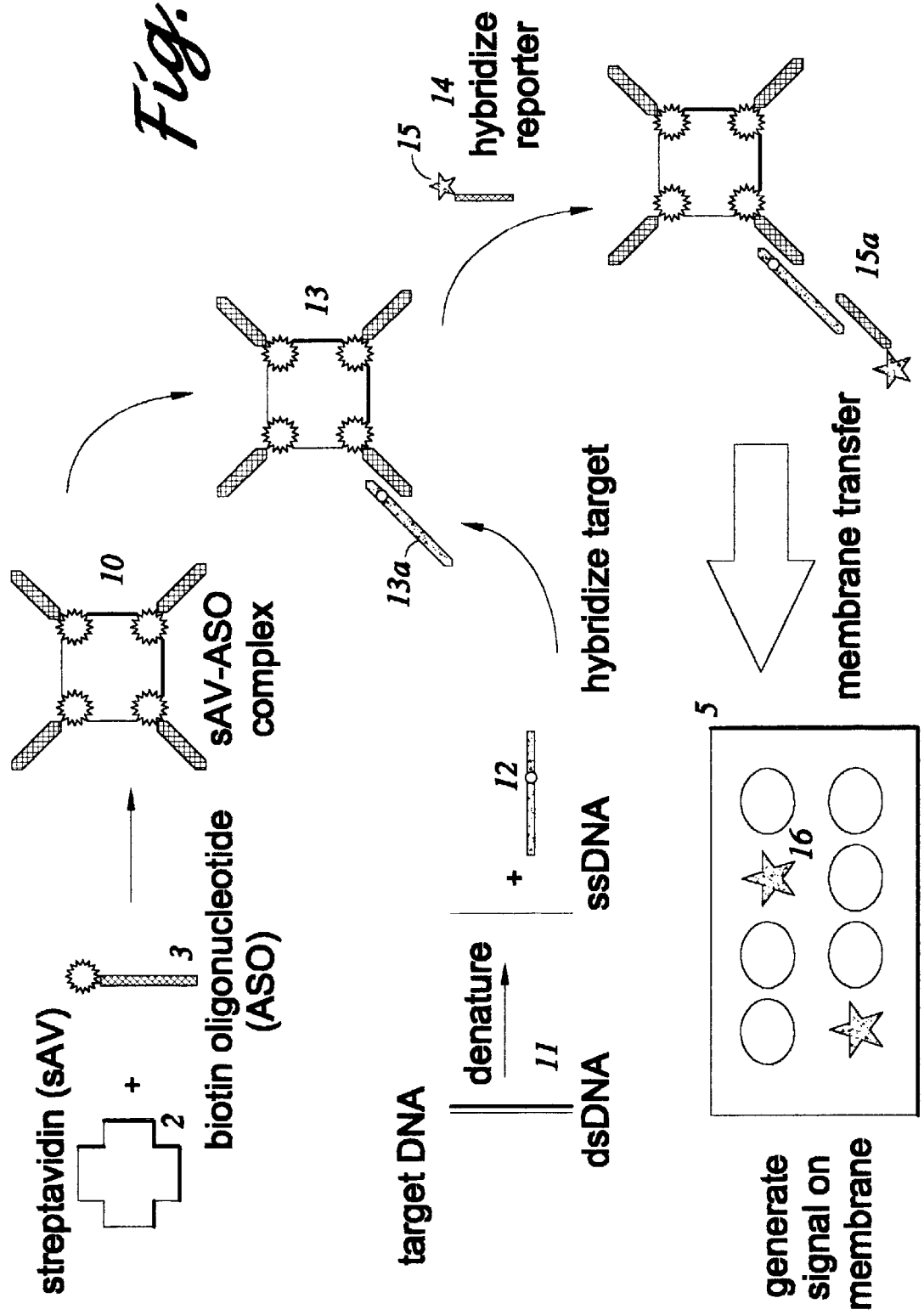
FIG. 3 is a flow chart illustrating the use of a streptavidin-ASO probe-target-reporter complex in accordance with yet another embodiment of the method of the invention.

Yet another method of the present invention is outlined in FIG. 3 wherein the various steps of the method are illustrated. Generally, this method is useful for analyzing for the presence of target biomolecules in a sample and involves reacting a biomolecule binding protein with a biomolecule probe to form a biomolecule complex, the biomolecule probe being capable of specifically binding with the target biomolecule. Then contacting the biomolecule complex with the sample under conditions suitable for specifically binding any target biomolecule present in the sample with the biomolecule probe causes a second complex to form. Next reacting a second biomolecule having an attached reporter group with the second complex which is being capable of specifically binding with at least a portion of any bound target biomolecule results in the formation of a third complex. Then applying the third biomolecule complex to the surface of a carboxylated polyvinylidene fluoride membrane, causes the third biomolecule complex to become immobilized to the surface through the interaction of the carboxylated PVDF surface with the binding protein. The final step involves determining the presence of any target biomolecules specifically bound to the biomolecule probe by detecting the reporter group.

In a preferred embodiment of this method, streptavidin (2) is reacted in solution with biotinylated oligonucleotide probe, or allele specific oligonucleotide (ASO) (3) forming a streptavidin-ASO probe complex (10). In a separate reaction, sample target DNA (11) is denatured to form single stranded DNA (12) (when the target DNA is double stranded).

The single stranded DNA (12) hybridizes to the streptavidin-ASO complex (10) forming a streptavidin-ASO-DNA complex (13). The oligonucleotide probe ASO is designed such that if the anticipated target DNA (11) hybridizes to the streptavidin-ASO probe (13) the resulting streptavidin-ASO-DNA complex includes a portion (a tail) of the target DNA which is not hybridized (13a). In order to determine the presence of any bound target DNA, a second oligonucleotide (14) having an attached reporter group (15) is added to the solution to form a streptavidin-ASO-DNA-reporter complex (15a). As shown, the second oligonucleotide containing a reporter group is hybridized to the tail or unhybridized portion of the target DNA of the complex (13). The solution is then applied to a carboxylated PVDF support (5) where only molecules containing streptavidin become immobilized to the support through the streptavidin carboxylated PVDF interaction. Any non hybridized oligonucleotide (14) containing reporter group (15) is easily washed from the PVDF support in a final wash step. A developing agent (16) is added to the site of adsorption on the PVDF support (5) to obtain a signal. Developing agents useful in the practice of the invention include alkaline phosphatase colorimetric reagents such as BCIP/NBT; chemiluminescent reagents such as dioxetanes or fluorescent reagents such as ELF); for horseradish peroxidase colorimetric reagents such as diaminobenzidine, amino ethylcarbazole or chloro naphthols and chemiluminescent reagents such as luminol/para-indophenol. Colloidal gold may be developed with silver stain.

The methods of the present invention may be better understood by reference to the following examples.

EXAMPLE 1

IMMOBILIZING BIOMOLECULES TO ACTIVATED CARBOXYLATED PVDF AND UTILIZING THE IMMOBILIZED BIOMOLECULES IN ANALYSIS PROCEDURES:

Preparing NHS Activated Carboxylated PVDF Membrane

A PVDF membrane available from Pall Corporation (under the tradename FluoroTrans G) was activated with an NHS active ester by placing the membrane in a slot blot device (commercially available from Bio-Rad) and filling each slot with 0.1M HC1. After allowing the membrane to soak for 15 minutes, the slots were rinsed with distilled water, followed by an anhydrous isopropyl alcohol (IPA) rinse. Each slot was then filled with a solution of 16 mM EDAC in IPA and incubated for 1 hour at 25° C. The slots were rinsed with IPA and then filled with a solution of 26 mM NHS in IPA solution and incubated for 1 hour at 25° C. Each slot was then rinsed with IPA and flushed with a solution of ice cold 10 mM sodium acetate at pH 4.5.

Attaching Amino-Ligands to Activated PVDF

The following were prepared for subsequent use in an attachment reaction:

1. A 16 mer (identified as A635) having the sequence 5'ACC AAA GAT GAT ATT T 3' (SEQ ID. NO:1) was synthesized using standard phosphoramidite synthesis chemistry on a Beckman Instruments Oligo 1000 DNA Synthesizer according to instrument use instructions. Beckman Binary-Pak phosphoramidites and associated synthesis reagents were used. An amino group was attached to the 5'terminus of the A635 oligonucleotide using the Uni-Link AminoModifier phosphoramidite reagent supplied by Clonetech of Palo Alto, Calif., according to manufacturer's instructions. A solution of A635 was prepared at 3 pmoles/μL in 50 mM sodium bicarbonate buffer at pH 8.5.

2. Streptavidin (sAV) (available from Zymed Laboratories, Inc. So. San Francisco, Calif.) solution at 0.5 mg/mL in bicarbonate buffer; and 3. Goat gamma globulin (available from Pel-Freez Biological, Rogers, Ariz.) at 0.4 mg/mL in bicarbonate buffer.
5. To selected slots or lanes of the device containing the activated PVDF membrane was applied 350 μL of one of the above solutions. The amount of active compound in each solution is as follows:
   1050 pmoles of 5' amino A635 oligonucleotide;
   0.175 mg streptavidin protein; and
   0.140 mg gamma globulin protein.

The slot device was then incubated 16.5 hours at 25° C. and the membrane containing immobilized oligonucleotide and proteins was subsequently rinsed with water and soaked in bicarbonate buffer for 20 minutes.

Hybridization of a Oligonucleotide Complementary to A635

An 18 mer oligonucleotide (A711) Complementary to A635 was synthesized using the Beckman Oligo 1000 DNA synthesizer according to manufacturer's instructions. The A711 Oligomer had the following sequence:

5' AAA TAT CAT CTT TGG TGT 3' (SEQ ID NO:2)
A711 was biotinylated at the 5'terminus using the Biotin-On reagent purchased from Clontech according to package instructions. A solution contain of the biotinylated oligonucleotide at a concentration of 122.8 pmoles in 250 μL of 6X buffer was prepared.

Figure 4:
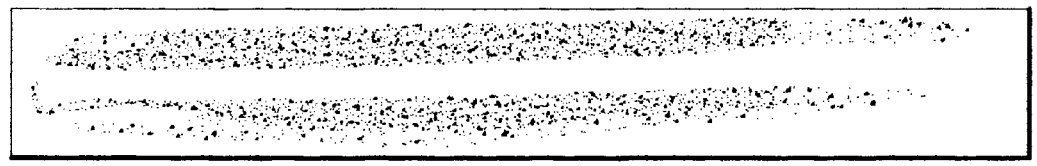
FIG. 4 is a reverse hybridization blot of covalently immobilized biomolecules on a carboxylated PVDF support.
Figure 4:
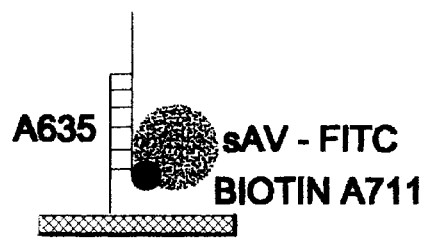
Figure 4:
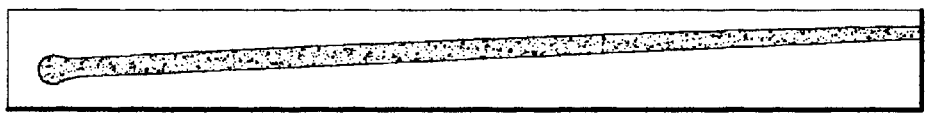
Figure 4:
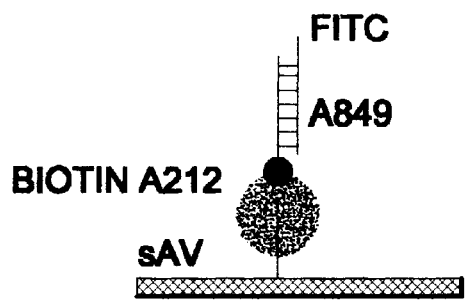

The lanes on the PVDF membrane containing immobilized A635 formed by applying the oligonucleotide solutions to selected slots were rinsed with water, followed by a 2X SSPE, 0.01%SDS rinse and finally 6X SSPE, 0.01%SDS pre-hybridization buffer rinse. The biotinylated A711 solution was then applied to the appropriate lanes on the membrane and the oligonucleotides were allowed to hybridize for 1 hour at 25° C. The slots were then rinsed with 2X buffer followed by applying a solution of 5.4 μg in 250 μL 2X buffer of streptavidin-FITC conjugate purchased from Zymed Laboratories. After a 1 hour incubation at 25° C. and rinse with 2X buffer, a fluorescent signal indicating that the streptavidin had bound to hybridized A711 was detected using a CCD camera. The camera used an excitation light source filtered at 485 nm and a camera emission filter at 530 nm. FIG. 4(a) shows the printer reproduction from the CCD camera positively illustrating the detection of immobilized oligonucleotide having hybridized complementary oligonucleotide.

Another detection technique was utilized in order to verify oligonucleotide attachment. The detection procedure was performed by rinsing the treated PVDF membrane in water and applying a DNA specific stain (purchased from In Vitrogen, San Diego). Developing the stain in DNA containing lanes according to manufacturer's directions resulted in the positive identification of DNA in the expected lanes.

Developing Immobilized Streptavidin

A solution of 0.2 μg Biotin-HRP conjugate (available from Pierce Chemical) in 350 μL of 2X buffer was applied to those lanes on the membrane expected to have immobilized streptavidin. After incubating the membrane for 1.5 hours at 25° C., it was rinsed with 2X buffer. Peroxidase colorimetric developing agent (TURBO TMB ELISA reagent purchased from Pierce Chemical) was then applied and an immediate signal response was obtained demonstrating the presence of streptavidin on the PVDF surface.

Development of Gamma Globulin Lanes

The PVDF membrane with immobilized protein and DNA was removed from the device and rinsed extensively in 0.15M NaCl. A protein colorimetric developing agent (BCA purchased from Pierce Chemical) was then applied over the entire area of the membrane. The developed stain positively showed protein in the expected protein containing portions of the PVDF membrane only.

Non-Covalent Coupling of a Biotinylated Oligonucleotide to Streptavidin Lanes

1. A 18 mer (identified as A212) having the sequence 5' AAA TAT CAT CTT TGG TGT 3' (SEQ ID. NO:2) was synthesized using standard phosphoramidite synthesis chemistry on a Beckman Instruments Oligo 1000 DNA Synthesizer according to instrument use instructions. Beckman Binary-Pak phosphoramidites and associated synthesis reagents were used. Biotin was attached to the 5'terminus of the A212 oligonucleotide using the Biotin-On phosphoramidite reagent supplied by Clonetech of Palo Alto, Calif., according to manufacturer's instructions. A solution of A212 was prepared at 126.7 pmoles in 250 μL of 2X buffer.

The A212 solution was applied to the expected streptavidin containing area of the PVDF membrane. The membrane was incubated 1 hour at 25° C. and then rinsed in 2X buffer and equilibrated in 6X buffer.

An 18 mer oligomer (A849) complementary to A212 and having the sequence 5' ACA CCA AAG ATG ATA TTT 3' (SEQ ID NO:3) was prepared as described above for A212. FITC was attached to the 5'terminus of the A849 oligonucleotide using the Fluorescein-ON phosphoramidite reagents purchased from Clontech. A solution of A849 was prepared having 116.4 pmoles per 250 μL of 6X buffer. This solution was applied to the membrane and allowed to hybridize to the expected A212 oligonucleotide for 1.5 hours at 25° C. The appropriate membrane areas were then rinsed 2X buffer and a fluorescent signal was then detected using a CCD camera as previously described. FIG. 4(b) illustrates s printer reproduction from the CCD camera positively illustrating the detection of immobilized oligonucleotide having hybridized complementary oligonucleotide.

These results demonstrated that either covalent attachment of oligonucleotides (via activated ester condensation with e.g. a 5' amino-oligonucleotide) or non-covalent attachment (via biotin-oligonucleotide binding to streptavidin) may be used to prepare a reverse hybridization blot on carboxylated PVDF membrane.

EXAMPLE 2

NON-COVALENT IMMOBILIZATION OF STREPTAVIDIN AND OLIGONUCLEOTIDE COMPLEX

The following reagents were prepared for immobilization:
1. A streptavidin-oligonucleotide complex, sAV-A212 oligonucleotide was prepared by mixing 5 μL of the biotin A212 oligonucleotide prepared in Example 1 (914 pmoles) with 120 μL of streptavidin (60 μg) in bicarbonate buffer and incubating the solution for 2 hours at 25° C.
2. A streptavidin (sAV) solution was prepared by dissolving 125 μg streptavidin (purchased from Zymed) in 250 μL bicarbonate buffer.
3. A 5'biotin oligonucleotide A212 solution was prepared by mixing 914 pmoles of the 5'biotin A212 prepared in Example 2 in 250 μL bicarbonate buffer The above described reagents were applied to a dry carboxylated PVDF membrane assembled in a slot blot device (purchased from Bio-Rad) as follows:
   10 μL of solution 1. (streptavidin-oligonucleotide (sAV-A212) complex to device slots E2 . . . E6; F2 . . .F6;
   10 μL solution 2. (sAV) to slots A2, A4 . . . C2,C4. (The device was incubated for 1 hour at 25° C. prior to adding the following solutions)
   10 μL solution 3. (5'biotin A212) to slots A2, A4. C2,C4. (These slots were previously treated with solution 2. (sAV)).
   10 μL solution 2. (sAV) to slots A6 . . . C6. The device was then incubated an additional 1 hour at 25° C.

The treated membrane was removed from the device and rinsed extensively in 2X buffer, then re-equilibrated in 6X buffer.

The equilibrated membrane was then treated over its entire surface with 1795 μL of the 5' labeled FITC oligonucleotide A849 prepared as described above. The A849 Oligonucleotide is complementary to the A212 oligonucleotide. The samples were then rinsed in 2X buffer. Fluorescent signals indicating any hybridized or nonspecifically absorbed A849 oligonucleotides were then detected using a CCD camera as previously described.

Figure 5:
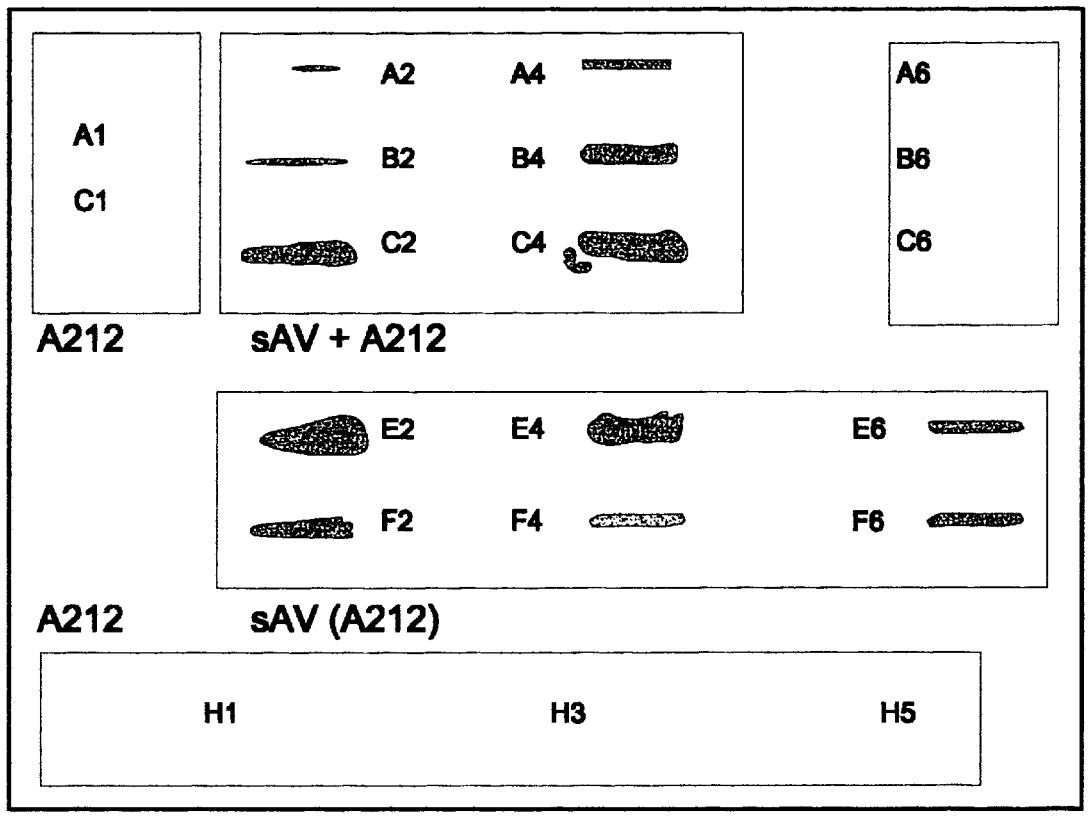
FIG. 5 is a reverse hybridization blot of non-covalently immobilized streptavidin-oligonucleotides on carboxylated PVDF.

FIG. 5 illustrates those slots of the device in which the A849 oligonucleotide is positively identified. Preliminarily, it is noteworthy that no binding was observed in slot A1, C1, H1, H3 demonstrating that 5' biotinylated oligonucleotide A212 does not non-specifically bind to the carboxylated PVDF membrane. Additionally, because no signal was detected in slot A6 . . . C6, A1, C1, H1, H3, and H5, the 5' FITC labeled A849 does not non-specifically bind to the PVDF membrane. Significantly, the 5° FITC-oligonucleotide A849 (complementary to oligonucleotide A212) hybridized only to slots containing immobilized A212 ( slots A2,A4 . . . C2,C6 and E2,E6 . . . F2,F6). Thus, the fluorescence CCD signal demonstrates that streptavidin-oligonucleotide complex (slots E2,E6 . . . F2,F6) and streptavidin that is first immobilized on the surface followed by non-covalently finding biotin-oligonucleotide (slots A2,A4 . . . C2,C4) are capable of achieving specific hybridization. Finally, this work demonstrates that covalent attachment of streptavidin is not required to prepare the reverse hybridization blot on carboxylated PVDF. The streptavidin will non-covalently immobilize to the support.

EXAMPLE 3

SOLUTION HYBRIDIZING A TARGET AMPLICON TO A STREPTAVIDIN-ASO PROBE AND SUBSEQUENTLY CAPTURING THE STREPTAVIDIN-ASO-TARGET COMPLEX WITH A CARBOXYLATED PVDF MEMBRANE

The following work demonstrates the utility of PVDF membranes in detecting Harvey (H)-ras mutations (proto-oncogenes associated with human urinary bladder carcinoma). The experiment utilized a 109 bp amplicon derived from the plasmid pEJ6.6 containing a GGC→GTC point mutation at codon 12 in Ras oncogene exon 1 (Saito, S., 1992, Keio J. Med 41: 80:86). The specific template DNA (from samples obtained from the Laboratory for Genetic Services, Houston, Tex.) was amplified using PCR protocols essentially as described by Saito using a Perkin-Elmer Cetus GeneAmp DNA Amplification Reagent Kit with AmpliTaq and following the manufacturer's instructions. 5'biotinylated reverse primers (identified below in Table I and graphically shown in the 109 bp antisense and sense strands below) for PCR were synthesized on an Oligo 1000 as described above. The forward primer was prepared without a reporter label. The resulting PCR amplicon having a 5'biotinylated anitsense strand was used without purification. The PCR products were analyzed and confirmed by agarose submarine gel electrophoresis.

The 109 bp antisense strand and sense strand are as follows. (The underlined portion refers to the mutations; the bold portion identifies primers for PCR.)
5'Biotin CTC TAT AGT GGG GTC GTA TTC GTC CAC AAA ATG GTT CTG GAT CAG CTG GAT GGT CAG CGC ACT CTT GCC CAC ACC GC(A)C GGC GCC CAC CAC CAC CAG CTT ATA TTC CGT C 3' (SEQ ID NO:8)
5' GAC GGA ATA TAA GCT GGT GGT GGT GGG CGC CGG(T) CGG TGT GGG CAA GAG TGC GCT GAC CAT CCA GCT GAT CCA GAA CCA TTT TGT GGA CGA ATA CGA CCC CAC TAT AGA G 3' (SEQ ID NO: 9)

The following Table I identifies sAV-ASO sequences used in this experiment. The first column identifies the sAV-ASO by a reference number which is referred to in the discussion below; the second column provides probe sequence information, the probes being labeled with streptavidin utilizing reagents purchased from Clontech as previously described; and the third column provides specificity information

TABLE I

| | | |
|---|---|---|
| A906 | 5'B—ACA—CCG—CCG—G (SEQ ID NO:4) | ASO binds WT sense strand at codons 12/13 |
| A907 | 5'B—ACA—CCG—ACG—GC (SEQ ID NO:5) | ASO binds Mutant sense strand at codons 12/13 |
| fwd20001 | 5'B—GAC—GGA—ATA—TAA—GCT—GGT—GG (SEQ ID NO:6) | forward primer; binds w/antisense; PCR makes sense strand (unlabeled in amplicon) |
| rev20002 | 5'B—CTC—TAT—AGT—GGG—GTC—GTA—TT (SEQ ID NO:7) | reverse primer; binds w/sense; PCR makes antisense strand (labeled in amplicon) |

The H-ras PCR amplicon (biotinylated antisense mutation strand) was denatured by heat and 20 μL of the amplicon solution was mixed with 180 μL of hybridization buffer. Then 10 μL of this solution was added to 60 μL solutions of each of the sAV-ASO probes identified above and incubated for 1 hour at 25° C.

After the incubation, each of the resulting solutions containing amplicon-sAV-probe complexes or amplicons which did not form sAV probe complexes (the solutions representing approximately 1 μL or 5% of the original amplicon stock) was then applied to separate wells of a microtiter plate. Each microtiter plate well contained carboxylated PVDF welded in place at its interior bottom. Each applied solution was immediately vacuum filtered and rinsed with wash buffer. Then each well was incubated with streptavidin-alkaline phosphatase conjugate for 1 hour. Following an extensive buffer rinse, signals indicating that the strepavidin-alkaline phosphatase had complexed with a biotinylated molecule in a complex were developed using a chemiluminescent reagent with CCD detection. The results of this experiment are outlined in Table II.

TABLE II

| sAV-ASO | Relative Signal* | Explanation |
|---|---|---|
| A906 | 1.1 | No Signal - Binds WT sense strand but not Mutant sense strand; No signal expected since no wild type present. |
| A907 | 3.5 | Binds Mutant sense strand which is unlabeled. However, primer region available to bind the biotin labeled antisense strand to form a sandwich assay generated signal. |
| fwd20001 | 2.6 | Binds antisense strand at primer site. Since antisense strand labeled signal is produced. |
| rev20002 | 7.6 | Binds sense strand at primer site. Can form sandwich with remainder of antisense strand which is labeled to generate signal. |

*Signal above background

Figure 6:
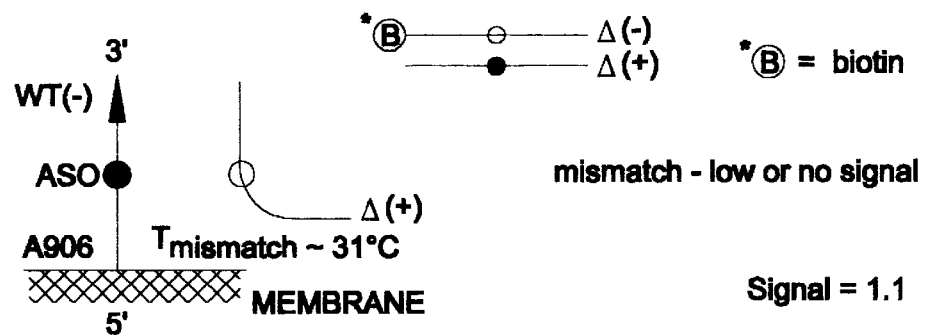
FIG. 6 illustrates examples of non-covalently immobilized streptavidin-oligonucleotides, complexes formed with the immobilized streptavidin oligonucleotides and their detection.
Figure 6:
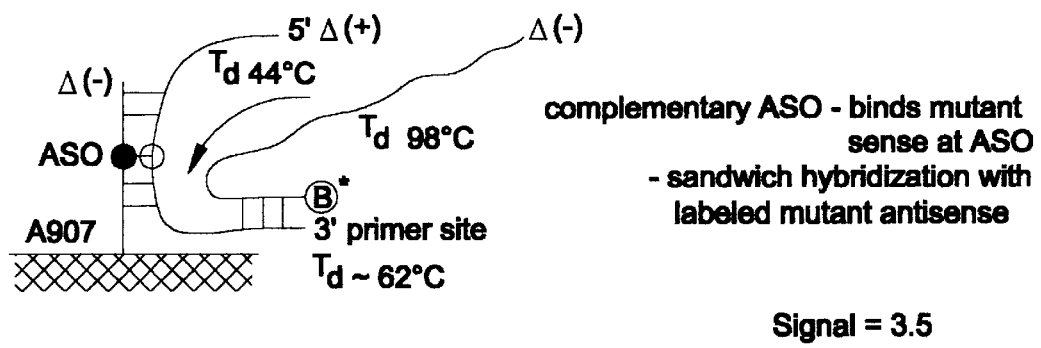
Figure 6:
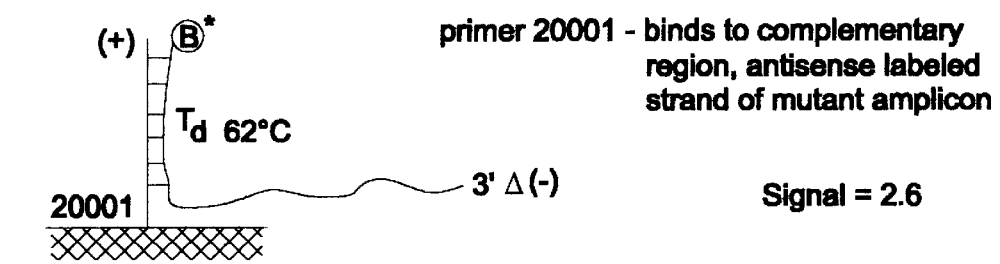
Figure 6:
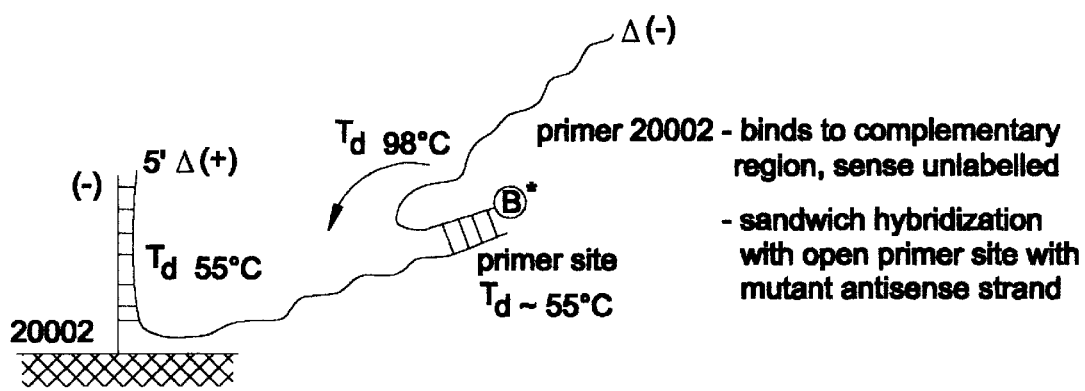

FIG. 6 graphically demonstrates the relevant interaction of solution components with the surface of the carboxylated PVDF membrane. In the case of the solution containing the sAV-ASO A906, because the A906 will bind to the wild type sense strand and only the antisense strand contains a label no signal is observed. In the case of the sAV-ASO A907, this ASO binds to the mutant sense strand which is unlabeled. However, because the mutant sense strand contains a tail at the 3' end primer site which hybridizes with the reporter labeled mutant sense strand a sandwich type hybridization occurs in the solution. The whole complex becomes immobilized to the carboxylated PVDF surface and detected during the detection step. The primer 20001 sAV-ASO binds to its complementary region on the reporter labeled antisense strand of the mutant amplicon. Thus, when the solution containing the sAV-ASO-mutant sense strand complex immobilizes to the surface of the carboxylated PVDF membrane it is detected during the final detection step. Finally in the case of the sAV-ASO 20002 primer, this ASO binds to a complementary region on the unlabeled sense strand. However, a sandwich complex is formed by the 3' primer site on the unlabeled sense strand with the reporter labeled mutant anti sense strand, thus providing a strong positive signal during the detection step.

The above example clearly demonstrates the surprisingly strong interaction observed between streptavidin-ASO oligonucleotides and carboxylated PVDF surfaces. Such an interaction provides numerous possibilities for such surfaces in the analysis of biomolecules and biomolecule complexes. It will be appreciated by persons skilled in the art that the present invention is not limited to what has been shown and described hereinabove, nor the dimensions of sizes of the physical implementation described immediately above.

BIBLIOGRAPHY

1. Southern, E. M., Detection of specific sequences among DNA fragments separated by gel electrophoresis, J. Mol. Biol. 98, 503–517 (1975)
2. Alwine, J. C., et al., Method for detection of specific RNAs in agarose gels by transfer to diazobenzyloxymethyl-paper and hybridization with DNA probes, Proc. Natl. Acad. Sci, 74:5350–5354 (1974)
3. Alwine, J. C., et al., Detection of specific RNAs by fractionation in gels and transfer to diazobenzyloxymethyl paper, Methods Enzymol., 68:220–242 (1979)
4. Southern, E. M., International Patent Application PCT GB 89/00460 (1988)
5. Bains, W., A novel method for nucleic acid sequence determination, J. Theoret. Biol., 135, 303–307 (1988)
6. Drmanac, R. et al., Sequencing of megabase plus DNA by hybridization: Theory of the Method, Genomics, 4, 114–128 (1989)
7. Lysov, Yu. P. et al., Determination of the DNA nucleotide sequence by hybridization with oligonucleotides. A new method. Proc. USSR Acad. Sci., 303, 1508–1511 (1988).
8. Khrapko, K. R. et al., An oligonucleotide hybridization approach to DNA sequencing. FEBS Lett 256, 118–122 (1989).
9. Southern, E. M. et al., Analyzing and comparing nucleic acid sequences by hybridization to arrays of oligonucleotides: Evaluation using experimental models Genomics, 13, 1008–1017 (1992).
10. Fodor, S.P.A. et al., Light Directed, spatially addressable parallel chemical synthesis. Science, 251, 767–773 (1991).
11. Cros. P. et al., Oligonucleotide genotyping of HLA polymorphism on microtitre plates. Lancet, 340, 870–873 (1992).
12. Saiki, R. K., et al., Genetic analysis of amplified DNA with immobilized sequence-specific oligonucleotide probes. Proc. Natl. Acad. Sci. USA, 86 6230–6234 (1989).
13. Rasmussen, S. E. et al., Covalent immobilization of DNA onto polystyrene microwells; the molecules are only bound at the 5 end. Anal. Biochem., 198. 138–142 (1991).
14. Lund, V. et al., Assessment of methods for covalent binding of nucleic acids to magnetic beads. Dynabeads and the characteristics of the bound nucleic acids in hybridization reactions. Nucleic Acids Res., 22. 10861–10880 (1988).
15. Khrapko K. R., et al. A method for DNA sequencing by hybridization with oligonucleotide matrix. J. DNA Sequencing Mapping, 1. 375–378 (1991).
16. Matson, R. S., et al. Biopolymer synthesis on polypropylene Supports. I. Oligonucleotides. Anal. Biochem, 217, 306–310 (1994).
17. Wehnert, M. S., et al. A rapid screening strip for tri- and dinucleotide short tandem repeats. Nucleic Acids Res., 22. 1701–1704 (1994).
18. Botstein, D., et al. Construction of a genetic linkage map in man using restriction fragment length polymorphisms. Amer. J. Hum. Genet., 32, 314–331.
19. The Huntington's Disease Collaborative Research Group. A novel gene containing a trinucleotide repeat that is expanded and unstable on Huntington's disease chromosomes. Cell, 72. 971–983 (1993).
20. Fu, Y.-H., et al. Variation of the CGG repeat at the fragile X site results in genetic instability: resolution of the Sherman paradox. Cell, 67. 1047–1055 (1991).
21. Kremer, E. J., et al. Mapping of DNA instability at the fragile X to a trinucleotide repeat sequence p(CCG)n. Science, 252, 1711–1714 (1991).
22. Verkerk, A.J.M.H. et al., Identification of a gene (FM<R-1) containing a CGC repeat coincident with a breakpoint cluster region exhibiting length variation in fragile X syndrome. Cell, 65, 905–914 (1991).

I claim:

1. A method of analyzing oligonucleotide targets comprising the steps; of:
    a) providing a solid support fabricated of carboxylated polyvinylidene fluoride, wherein the surface of the carboxylated polyvinylidene fluoride has carboxyl groups;
    b) immobilizing a binding protein by non-covalent interaction of the binding protein with the surface;
    c) attaching oligonucleotide probes to the support, said probes having a specific binding partner to said binding protein, whereby the oligonucleotide probes are bound to the surface of the support via a binding protein-specific binding partner interaction between the specific binding partner and the binding protein;
    d) applying oligonucleotide targets to the surface under hybridizing conditions; and
    e) determining if hybridization occurs thereby detecting the presence or absence of oligonucleotide targets having sequences complementary to the oligonucleotide probes.

2. The method of claim 1, wherein said binding protein is selected from the group consisting of streptavidin and avidin and the specific binding partner is biotin.

3. The method of claim 1 wherein the oligonucleotide targets include an attached reporter group.

4. The method of claim 3 wherein the reporter group is selected from the group consisting of chemiluminescent compounds, enzymes, fluorescent compounds, metal complexes, haptens and radioluminescent compounds.

5. A method for analyzing the presence of target biomolecules in a sample, the method comprising the steps of:
    a) reacting a biomolecule binding protein with a biomolecule thereby forming a biomolecule complex, the biomolecule being capable of specifically binding with the target biomolecule;
    b) applying the biomolecule complex to a substrate fabricated of carboxylated polyvinylidene fluoride, wherein the surface of the carboxylated polyvinylidene fluoride has carboxyl groups, thereby forming an immobilized biomolecule complex;
    c) applying the sample to the immobilized biomolecule complex; and
    d) detecting the presence of target biomolecules specifically bound to the biomolecule.

6. The method of claim 5 wherein said biomolecule is an oligonucleotide.

7. The method of claim 6 wherein said oligonucleotide is a biotinylated oligonucleotide.

8. The method of claim 6 wherein said biomolecule binding protein is selected from the group consisting of avidin and streptavidin.

9. A method of analyzing for the presence of target biomolecules in a sample, the method comprising the steps of:
    a) reacting a biomolecule binding protein with a biomolecule probe thereby forming a first biomolecule complex, the biomolecule probe being capable of specifically binding with the target biomolecule;
    b) contacting the first biomolecule complex with the sample under conditions suitable for specifically binding any target biomolecule present in the sample with the biomolecule probe, thereby forming a second complex;
    c) reacting a second biomolecule having an attached reporter group, with the second complex, the second biomolecule being capable of specifically binding with at least a portion of any bound target biomolecule, thereby forming a third complex;
    d) applying the third biomolecule complex to a substrate fabricated of carboxylated polyvinylidene fluoride, wherein the surface of the carboxylated polyvinylidene fluoride has carboxyl groups, thereby forming an immobilized third biomolecule complex; and
    d) determining presence of any target biomolecules specifically bound to the biomolecule probe by detecting the reporter group.

10. The method of claim 9 wherein said biomolecule probe, said biomolecule target and the second biomolecule are oligonucleotides.

11. The method of claim 10 wherein said biomolecule probe is biotinylated oligonucleotide.

12. The method of claim 11 wherein said biomolecule binding protein is selected from the group consisting of avidin and streptavidin.

13. The method of claim 9 wherein detecting the reporter group is accomplished by applying a developing agent to the immobilized third biomolecule complex.

14. The method of claim 13 wherein said developing agent is selected from the group consisting of phosphatase colorimetric agents, chemiluminescent agents, horseradish peroxidase colorimetric agents and dyes.

15. The method of claim 9 wherein the reporter group is a fluorescing group.

16. A reagent for analyzing biomolecules, the reagent comprising:
    a) a carboxylated polyvinylidene fluoride support having carboxyl groups; and b) immobilized biomolecules, wherein at least one of said immobilized biomolecules comprises a binding protein non-covalently attached to the support.

17. The reagent of claim 16 wherein the immobilized biomolecules are biomolecule complexes formed of the biomolecule and a binding protein.

18. The reagent of claim 17 wherein the biomolecule is a biotinylated oligonucleotide and the binding protein is selected from the group consisting of avidin and streptavidin.

19. A reagent for analyzing biomolecules, the reagent comprising:

a) a solid support fabricated of carboxylated polyvinylidene fluoride wherein the surface of the carboxylated polyvinylidene fluoride has carboxyl groups, and b) oligonucleotide probes covalently attached to the support.

20. A method of analyzing oligonucleotide targets comprising the steps of:

a) providing a solid support fabricated of carboxylated polyvinylidene fluorides wherein the surface of the carboxylated polyvinylidene fluoride has carboxyl groups, and wherein the solid support has oligonucleotide probes covalently bound to the surface;

b) applying oligonucleotide targets to the surface under hybridizing conditions; and c) determining if hybridization occurs thereby detecting the presence or absence of oligonucleotide targets having sequences complementary to the oligonucleotide probes.

* * * * *